United States Patent
Buza et al.

(10) Patent No.: US 11,871,941 B2
(45) Date of Patent: Jan. 16, 2024

(54) PATIENT-SPECIFIC CUTTING GUIDE FOR THE SHOULDER

(71) Applicant: Howmedica Osteonics Corp., Mahwah, NJ (US)

(72) Inventors: Luke Buza, Flemington, NJ (US); Gennaro A. Barile, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 45 days.

(21) Appl. No.: 17/462,083

(22) Filed: Aug. 31, 2021

(65) Prior Publication Data

US 2021/0386435 A1 Dec. 16, 2021

Related U.S. Application Data

(63) Continuation of application No. 15/055,109, filed on Feb. 26, 2016, now Pat. No. 11,134,963, which is a
(Continued)

(51) Int. Cl.
*A61B 17/16* (2006.01)
*A61B 17/15* (2006.01)
(Continued)

(52) U.S. Cl.
CPC .......... *A61B 17/1684* (2013.01); *A61B 17/15* (2013.01); *A61B 17/1778* (2016.11);
(Continued)

(58) Field of Classification Search
CPC ............ A61B 17/1684; A61B 17/1664; A61B 17/1666; A61B 17/1668
See application file for complete search history.

(56) References Cited

U.S. PATENT DOCUMENTS 2,012,007 A 8/1935 August
5,800,551 A 9/1998 Williamson et al.
(Continued)

OTHER PUBLICATIONS

International Search Report and Written Opinion for Application No. PCT/US2012/040831 dated Dec. 11, 2012.
(Continued)

*Primary Examiner* — Si Ming Ku
(74) *Attorney, Agent, or Firm* — Lerner David LLP

(57) ABSTRACT

Disclosed herein are patient-specific cutting guides for guiding a surgical instrument for resecting a portion of a glenoid of a patient. The cutting guides include a base portion having a contact surface shaped to substantially match at least a portion of a cavity of the glenoid. The base portion has a guide hole extending therethrough in which the guide hole has an axis coaxial with an axis of rotation. The cutting guides include one or more stabilization members extending outwardly from the base portion and having a contact surface shaped to substantially match an outer surface of a portion of a scapula of the patient. The stabilization members are oriented to take into account the patient's anatomy in orienting and stabilizing the guide with respect to the glenoid. The guide hole of the base portion is for guiding the surgical instrument to create a guide hole in the glenoid.

17 Claims, 8 Drawing Sheets

Related U.S. Application Data continuation of application No. 14/124,422, filed as application No. PCT/US2012/040831 on Jun. 5, 2012, now Pat. No. 9,301,768.

(60) Provisional application No. 61/494,579, filed on Jun. 8, 2011.

(51) Int. Cl.
    *A61B 17/17*     (2006.01)
    *G16H 50/50*     (2018.01)
    *A61B 34/10*     (2016.01)
    *A61B 90/00*     (2016.01)

(52) U.S. Cl.
    CPC ........ *G16H 50/50* (2018.01); *A61B 2034/108* (2016.02); *A61B 2090/033* (2016.02); *Y10T 29/49* (2015.01)

(56) References Cited

U.S. PATENT DOCUMENTS

| | | |
|---|---|---|
| 6,129,764 A | 10/2000 | Servidio |
| 6,364,910 B1 | 4/2002 | Shultz et al. |
| 7,070,662 B2 | 7/2006 | Studebaker |
| 7,537,618 B2 | 5/2009 | Collazo |
| 7,604,665 B2 | 10/2009 | Iannotti et al. |
| 7,785,370 B2 | 8/2010 | Collazo |
| 7,785,371 B2 | 8/2010 | Collazo |
| 2004/0030245 A1 | 2/2004 | Noble et al. |
| 2005/0148843 A1 | 7/2005 | Roose |
| 2005/0245808 A1 | 11/2005 | Carson |
| 2006/0004373 A1 | 1/2006 | Ondrla et al. |
| 2006/0136058 A1 | 6/2006 | Pietrzak |
| 2008/0161815 A1 | 7/2008 | Schoenefeld et al. |
| 2008/0257954 A1 | 10/2008 | Naccache et al. |
| 2009/0110498 A1 | 4/2009 | Park |
| 2009/0157083 A1 | 6/2009 | Park et al. |
| 2010/0023015 A1 | 1/2010 | Park |
| 2010/0076563 A1 | 3/2010 | Otto et al. |
| 2010/0153081 A1 | 6/2010 | Bellettre et al. |
| 2010/0217270 A1 | 8/2010 | Polinski et al. |
| 2010/0305574 A1 | 12/2010 | Fitz et al. |
| 2010/0312160 A1 | 12/2010 | Creighton et al. |
| 2011/0015639 A1 | 1/2011 | Metzger et al. |
| 2011/0029088 A1 | 2/2011 | Rauscher et al. |
| 2011/0054478 A1 | 3/2011 | Vanasse et al. |
| 2011/0130795 A1 | 6/2011 | Ball |
| 2011/0190775 A1* | 8/2011 | Ure ................ A61F 2/4609 606/91 |
| 2012/0078258 A1 | 3/2012 | Lo et al. |
| 2012/0078259 A1 | 3/2012 | Meridew |
| 2012/0141034 A1 | 6/2012 | Iannotti et al. |
| 2012/0143267 A1* | 6/2012 | Iannotti ............. A61B 17/151 606/86 R |

OTHER PUBLICATIONS

Partial ISR dated Aug. 31, 2012 for PCT/US2012/040831.
U.S. Appl. No. 12/541,443, filed Aug. 14, 2009.

* cited by examiner

PATIENT-SPECIFIC CUTTING GUIDE FOR THE SHOULDER

CROSS-REFERENCE TO REALTED APPLICATIONS

This application is a continuation of U.S. application Ser. No. 15/055,109, filed Feb. 26, 2016, which is a continuation of U.S. application Ser. No. 14/124,422, filed on Jan. 29, 2014 and issued as U.S. Pat. No. 9,301,768 on Jun. 26, 2014, which claims the benefit of national phase entry under 35 U.S.C. § 371 of International Application No. PCT/US2012/040831 filed Jun. 5, 2012, published in English, which claims the benefit of the filing date of U.S. Provisional Application No. 61/494,579, filed Jun. 8, 2011, entitled, "Patient-Specific Cutting Guide For The Shoulder," the disclosures of which are hereby incorporated herein by reference.

FIELD OF THE INVENTION

The present invention relates to patient-specific cutting guides for the shoulder, and in particular it relates to such cutting guides having a patient-specific contact surface shaped to rest on bone in a predetermined manner, the guides having at least one guide hole or slot used to resect bone as preoperatively planned such that a corresponding implant can be located and oriented on the resected bone in a predefined manner.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in the case where tendons in a joint become lax or soft tissues in or adjacent the joint tear become damaged or worn.

Arthroplasty procedures can be used to repair damaged joints. During a typical arthroplasty procedure, an arthritic or otherwise dysfunctional joint can be remodeled or realigned, or an implant or implants can be implanted into the damaged region. Arthroplasty procedures may take place in any of a number of different regions of the body, such as a knee, a hip, a shoulder, or an elbow.

One type of arthroplasty procedure is a shoulder arthroplasty, in which a damaged shoulder joint is replaced with prosthetic implants. The shoulder joint may have been damaged by, for example, arthritis (e.g., severe osteoarthritis or degenerative arthritis), trauma, or a rare destructive joint disease.

Implants that are implanted into a damaged region may provide support and structure to the damaged region, and may help to restore the damaged region, thereby enhancing its functionality. Prior to implantation of an implant in a damaged region, the damaged region may be prepared to receive the implant. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation may be used for locating a position and orientation to resect the humeral head for proper humeral stem placement in the humerus.

Accuracy in implant alignment is an important factor to the success of the procedure. A one to two millimeter translational misalignment, or a one to two degree rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. Currently available instrument and tools do not always enable the surgeon to make the most accurate cuts on the bone surface in preparing the target joint for implantation. Thus, there remains a need for tools that improve the accuracy of the joint resurfacing process.

BRIEF SUMMARY OF THE INVENTION

Patient-specific cutting guides for resecting the humerus and glenoid in a preoperatively planned manner are described herein. These patient-specific guides are configured to allow a surgeon to accurately and quickly perform a shoulder arthroplasty procedure that substantially restores the natural alignment of the joint. Specifically, the patient-specific guides are shaped such that they matingly receive the regions of the bone to be subjected to a treatment (e.g., cutting, drilling, reaming, and/or resurfacing). The patient-specific guides are also shaped to provide the proper location and orientation of the treatment relative to the regions of the bone. The shaped aspect of the patient-specific guides allows the treatment of the bone regions to be done quickly and with a high degree of accuracy that will allow the implants to restore the patient's joint to a generally pre-deteriorated state.

The disclosed guides relate to a prosthetic device system for repairing ball-and-socket type joints in a human body, particular shoulder joints. Applicants incorporate by reference in its entirety herein the disclosure of U.S. Pat. No. 7,537,618 ("the '618 Patent"), which relates to a modular anatomic adjustable prosthetic device system for the shoulder and hip joints. U.S. Pat. Nos. 7,785,370 and 7,785,371 which claim priority to the '618 Patent, the disclosures of which are also incorporated by reference in their entirety herein.

DETAILED DESCRIPTION

Figure 1:
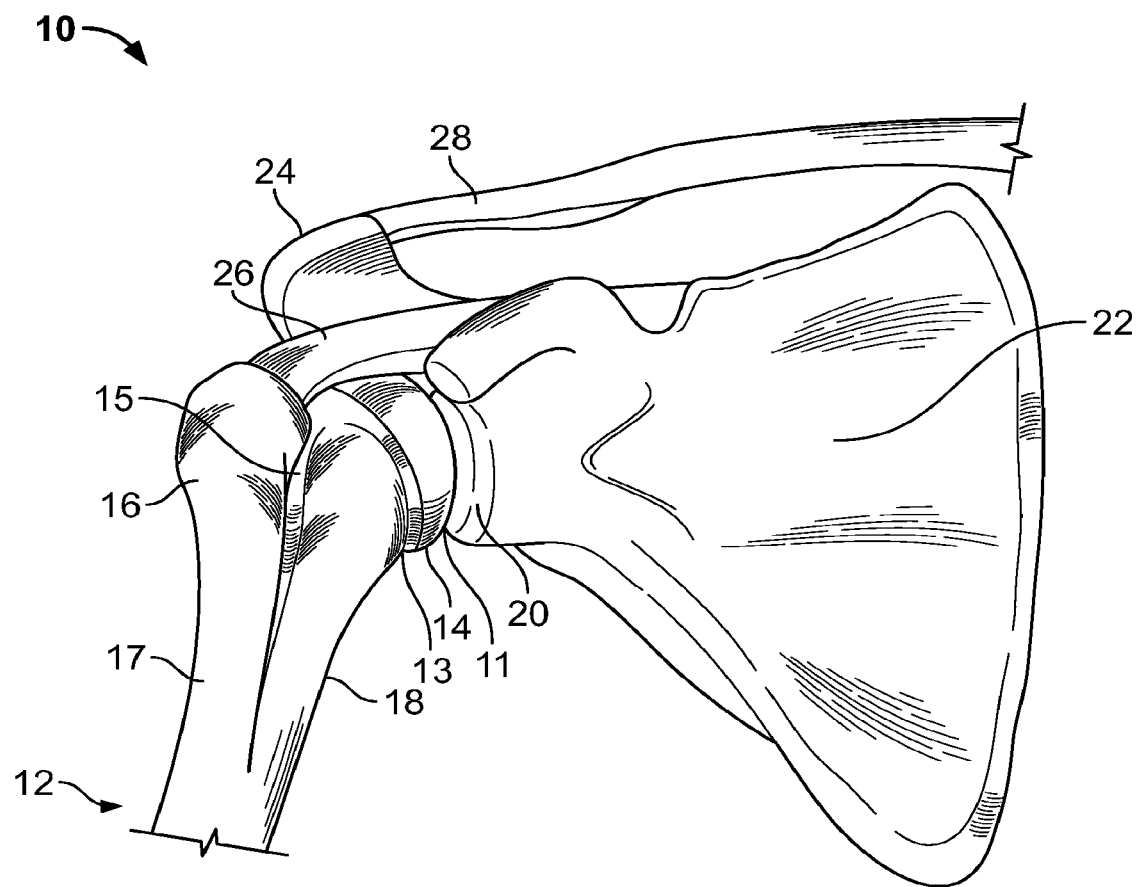
FIG. 1 shows the general shoulder joint anatomy of a patient.
Figure 2:
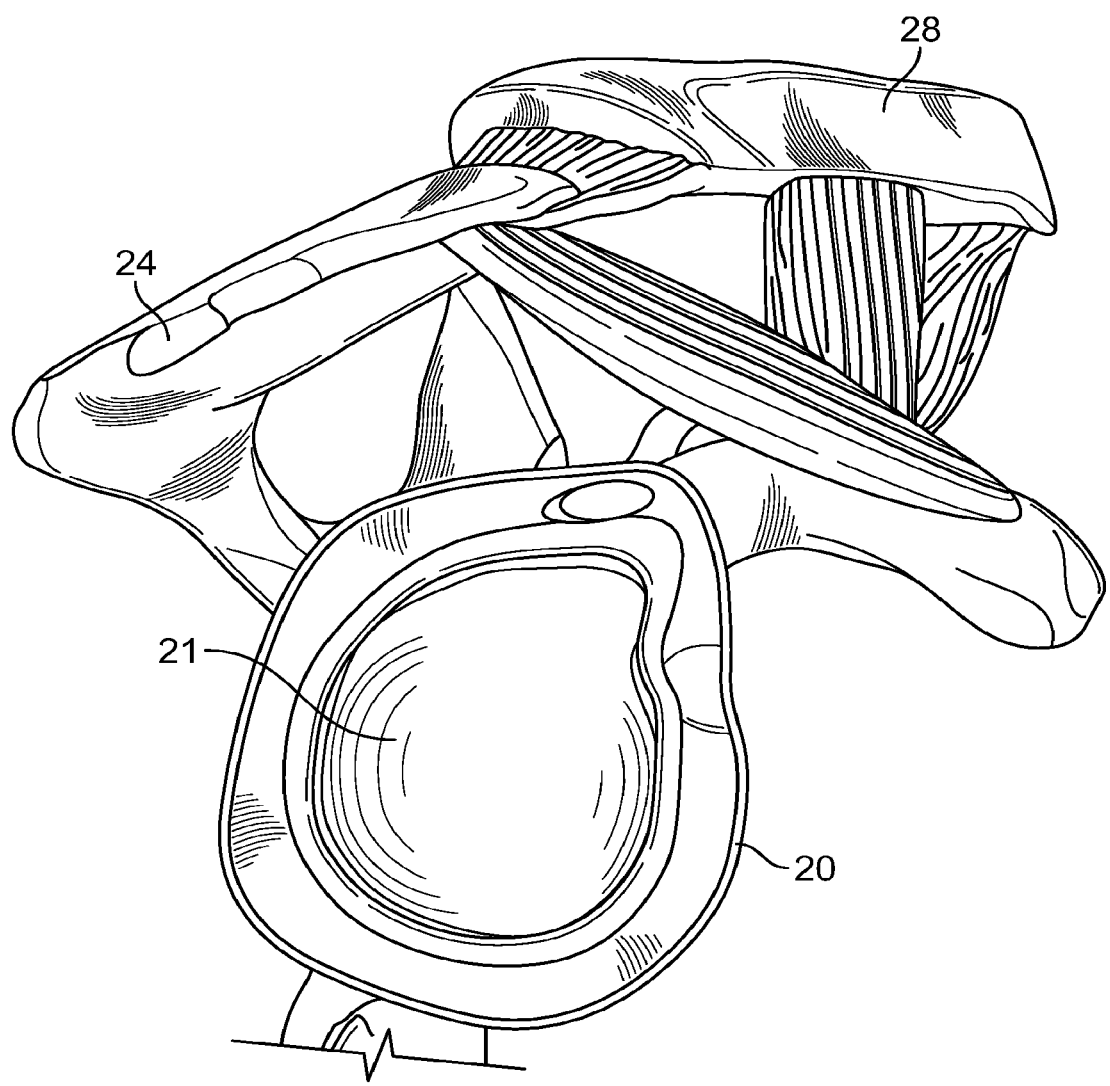
FIG. 2 is a view of a glenoid cavity of the shoulder joint.

FIG. 1 shows the general anatomy of shoulder joint 10 of a patient. Humerus 12 of joint 10 includes a neck portion 13, a head portion 14 and a shaft portion 17 having a greater tuberosity 16 and a lesser tuberosity 18. Between greater and lesser tuberosities 16, 18 is bicipital groove 15. As shown in FIGS. 1-2, scapula 22 terminates at glenoid 20 having a cavity 21 in which an outer surface 11 of head portion 14 rotates within. Along with humerus 12 and scapula 22, the acromion 24, rotator cuff 26 and clavicle 28 all provide support to the range of motion of the shoulder joint 10 of the patient.

Figure 3:
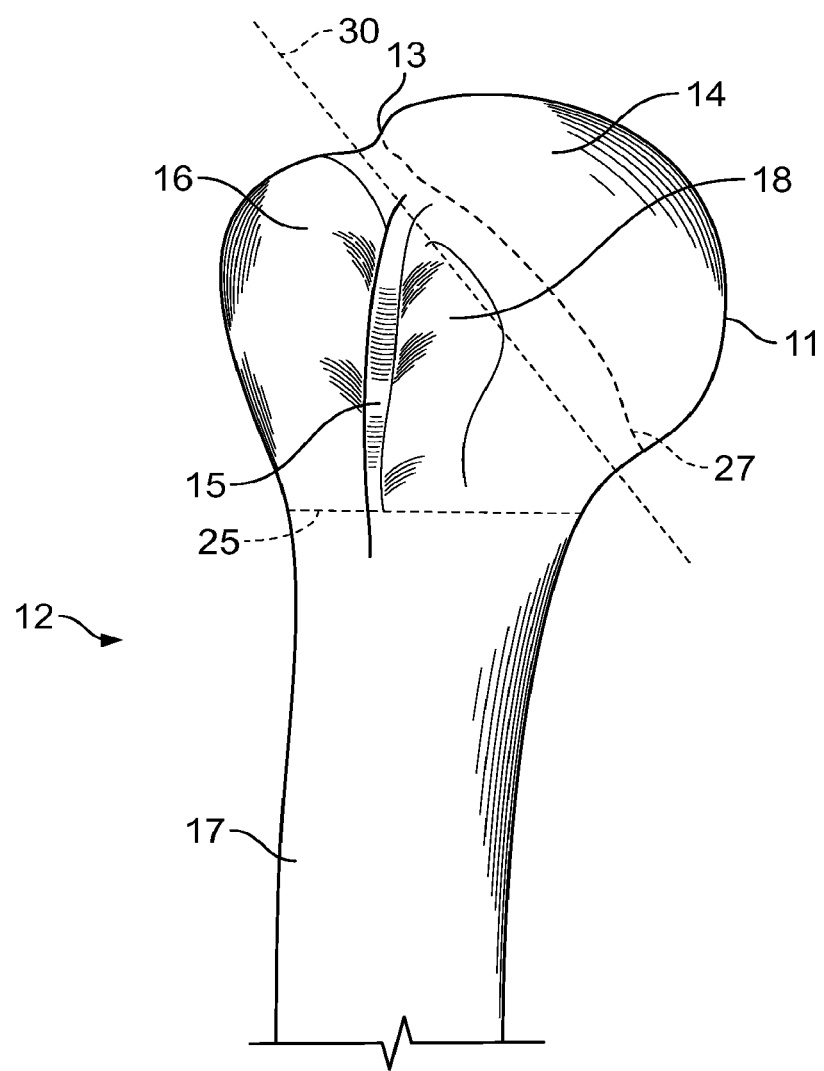
FIG. 3 is a posterior view of a proximal portion of a humerus of the shoulder joint showing a resection line adjacent the anatomical neck of a humerus, the resection line corresponding to the preoperatively planned location and orientation of a humeral stem component that will be implanted in a shoulder arthroplasty procedure.
Figure 4:
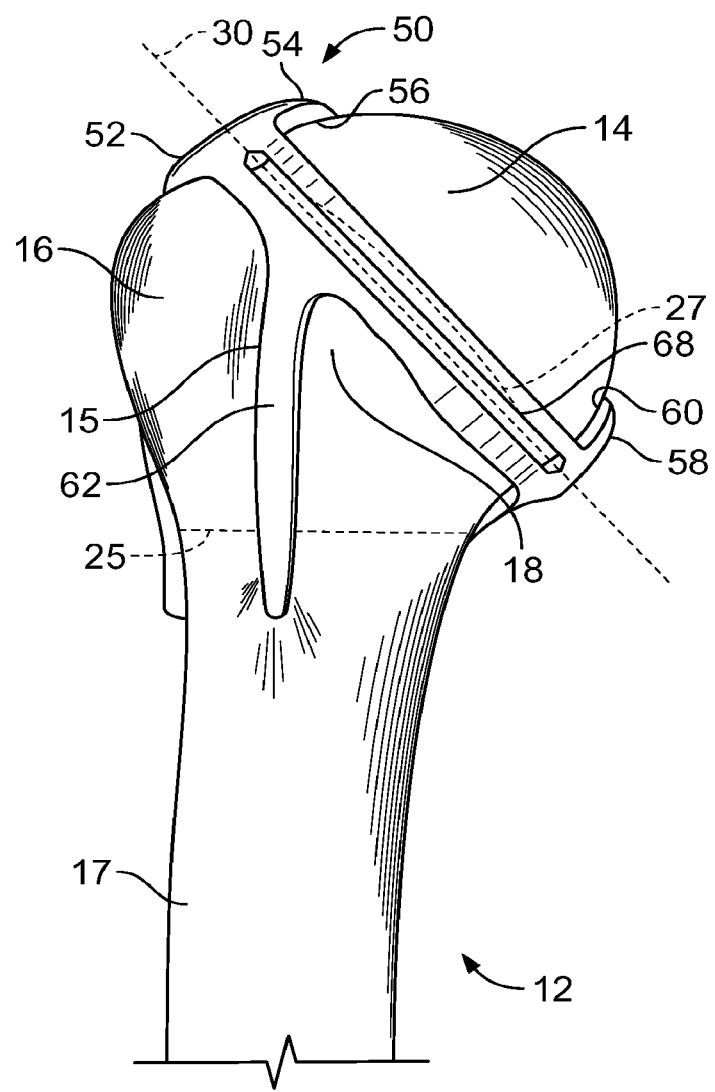
FIG. 4 is a view of an embodiment of a patient-specific cutting guide of the present invention for resecting the humerus.

FIG. 3 is a posterior view of a proximal portion of humerus 12 of shoulder joint 10. Head portion 14 includes outer surface 11. Also shown is bicipital groove 15, a substantially straight surcical neck line 25 and a curvy anatomical neck line 27. Outer surface 11, biciptal groove 15, substantially straight surcical neck line 25 and curvy anatomical neck line 27 are all anatomical features of humerus 12 that can be used to aid in the designing of one or more patient-specific contact surfaces that may be located a guide 50, for example, as shown in FIG. 4, and thereafter accurately locate guide 50 on humerus 12.

Prior to a total shoulder arthroplasty procedure being conducted, shoulder joint 10 is generally compromised through injury or general wear and tear. A compromised joint generally leads to range of motion difficulty and pain for the patient. In a joint 10 that is compromised, head portion 14 and/or glenoid cavity 21 may be degenerated such that the axis of rotation of the shoulder joint is not in the same location as it was prior to joint 10 being compromised.

The axis of rotation of the shoulder joint varies based upon the type of motion. For flexion and extension, the axis of rotation is a transverse axis though the center of the humeral head. For abduction and adduction, the axis of rotation is a sagittal axis thought the center of the humeral head. For internal and external rotation, the axis of rotation is a vertical axis though the center of the humeral head.

During a total shoulder arthroplasty procedure, the humerus is resected in order to receive a humeral stem component. In such a procedure, the humeral head is generally resected and the shaft of the humerus is reamed to receive the humeral stem component prosthesis. It is important that the humeral stem component be positioned in the correct location and orientation in order to restore the axis of rotation of joint 10. Some humeral stem components may include a flange that is adapted to contact a flat portion of resected bone of the humerus in order to correctly position and stabilize the humeral stem component within shaft 17 of humerus 12 such that the axis of rotation of joint 10 may be restored.

Also during a total shoulder arthroplasty procedure, the glenoid is resected in order to receive a glenoid component. In a shoulder arthroplasty procedure for implanting a reverse shoulder prosthesis, a cavity of the glenoid may be reamed and a guide hole may be drilled in order to receive a central screw extending outwardly from an outer contact surface of the glenoid component. The location and orientation of the guide hole may be based on the shape of the glenoid component, for example, such that the glenoid component can be implanted in the resected glenoid cavity and the axis of rotation of the joint may be restored. It is important that the glenoid component be positioned in the correct location and orientation in order to restore the axis of rotation of joint 10. The glenoid component preferably has an articular surface corresponding to an outer surface of a humeral head component which is engaged to the humeral stem component implanted at least partially within the shaft of the humerus. Generally, the glenoid component has a diameter that is approximately 6 mm in diameter larger than the humeral stem component.

As discussed above, humerus 12 must be resected at the correct location and orientation in order for a corresponding humeral stem prosthesis to be accurately implanted in shaft 17 of humerus 12 such that the axis of rotation of the shoulder joint may be restored. Thus, the location and orientation of resection line 30, as shown in FIG. 3, is preoperatively planned according to one aspect of the present invention. Resection line 30 corresponds to the location and orientation of resection slot 68 of guide 50, as shown in FIG. 4, once located and oriented on neck portion 11 and head portion 14 of humerus 12.

In order to preoperatively plan the location and orientation of slot 68 of guide 50, joint 12 first has to be scanned. After joint 10 is scanned using CT or MRI, for example, the images obtained from the scan are used to create a 3D model (not shown) of the shoulder joint. A technician preferably then selects certain points on the 3D model that the patient-specific cutting guide will contact with contact surfaces that match at least a portion of the area of the humerus surrounding the selected points. For instance, the technician may select points located on neck portion 13 of humerus and attach the points with splines. Once a line is created on neck portion 13, a patient-specific contact surface (not shown) on guide 50 is preferably created to substantially match the contour of the line such that guide 50, once manufactured, will contact the actual outer surface of humerus 12 in a predetermined location and orientation while being substantially stabilized thereto. Patient-specific cutting guide 50, as shown in FIG. 4, can be manufactured via SLA, milled from a jig blank, or molded, for example.

FIG. 4 shows patient-specific cutting guide 50 for guiding a surgical instrument, such as a saw blade (not shown) for resecting a portion of humerus 12. Guide 50 includes a base portion 52 having a contact surface shaped to substantially match an outer surface of a neck portion 13 of humerus 12. Guide 50 further includes at least one proximal stabilization member 54 extending medially from base portion 52 and having a contact surface 56 shaped to substantially match an outer surface 11 of a head portion 14 of humerus 12. Preferably, guide 50 also includes at least one distal stabilization member 53 extending distally from base portion 52 and having a contact surface shaped to substantially match an outer surface of a shaft portion 17 of humerus 12.

A generally reproducible feature on the humerus is bicipital groove 15, which contains the long head of the biceps tendon. The contact surface of the distal stabilization member 53 is shaped to match a location on the bicipital groove 15 of humerus 12. Another generally reproducible feature on the humerus is anatomic neck 27. The contact surface of base portion 52 of guide 50 is shaped to match a location either on or adjacent to anatomic neck line 27 of humerus 12. Preferably, guide 50 contacts bone on humerus 12 in at least three locations in order to substantially stabilize guide 50 when it is being used to resect humerus 12. Proximal stabilization member 54 as well as proximal stabilization member 58 having patient-specific contact surface 59 are preferably used in conjunction with distal stabilization member 53 in order to stabilize guide 50 sufficiently on humerus 12.

Guide 50 may also be pinned in place by placing pins through pin holes (not shown) in guide 50 preferably at some point along base portion 52. Preferably, base portion 52 of guide 50 includes two guide holes adapted to receive a stabilization pin therein for securing guide 50 to humerus 12. In one embodiment, guide 50 includes a first guide hole located on base portion 52 superior to guide slot 68 and a second guide hole located on base portion 52 anterior to guide slot 68.

Figure 5:
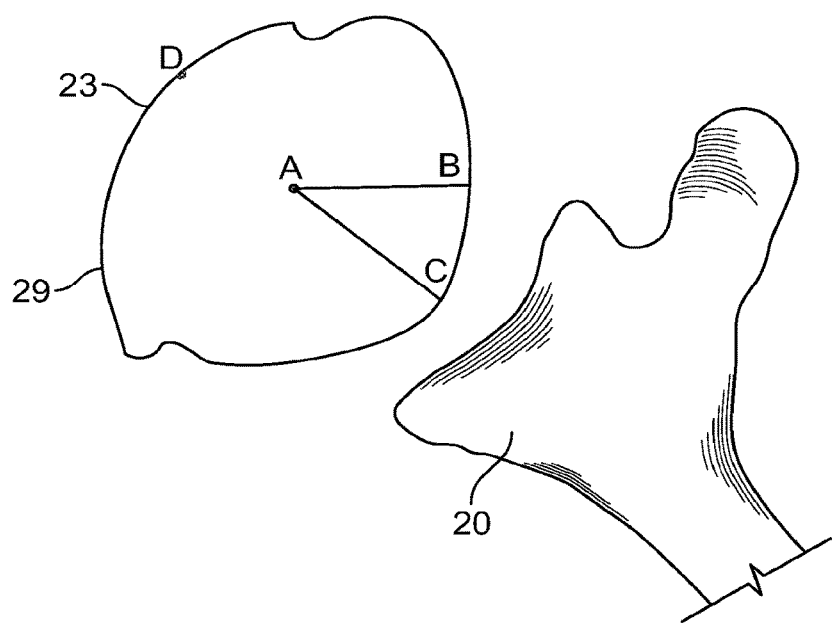
FIG. 5 is a top view of a humerus stem and glenoid.
Figure 9:
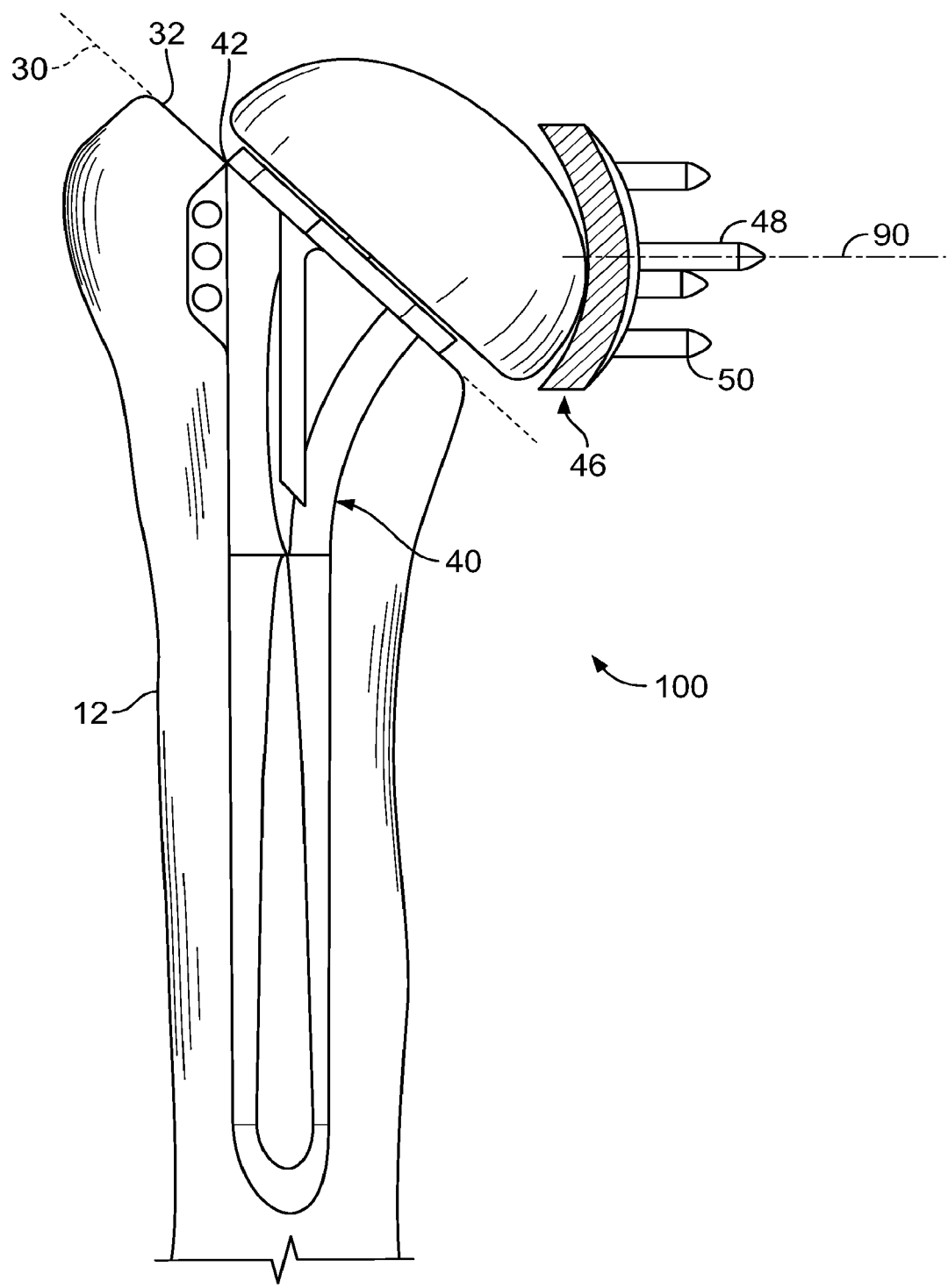
FIG. 9 is a view of a total shoulder arthroplasty prosthesis implant after a humerus and a glenoid of a patient has been resected to receive a humeral stem component and glenoid component, respectively.

Base portion 52 of guide 50 includes guide slot 68 for guiding the surgical instrument. Guide slot 68 is preferably located approximately 135° from a line perpendicular to a longitudinal axis of the humeral stem, also referred to as the neck-shaft angle that will be resected. The resected neck-shaft angle preferably matches the neck-shaft angle of the humeral stem component. The neck shaft angle may be greater or less than 135°, but preferably lies between a range of 110° and 160°. Guide slot 68 preferably produces a flat resection cut 32 as shown in FIG. 9 so that the version is dedicated. Humeral stem version is the positioning of the humeral stem in the correct position in the humeral canal when viewing from the top of humeral head 29 as shown in FIG. 5. Lateral side 23 of humeral head 29 is also shown in FIG. 5. If a stem is positioned with a trunion of the stem in the A-B direction, this would be 0° retroversion. A stem positioned in the A-C direction is at 30° of retroversion. Another way to find 30° of retroversion is to have the most lateral point on the stem position in line with point D which is 8-10 mm retroversion from the bicipital groove. Also, a recess is preferably reamed into shaft 17 of humerus 12 such that a humeral stem component can be implanted therein.

One method of making patient-specific cutting guide 50 for guiding a surgical instrument for resecting a portion of humerus 12, includes first obtaining image data associated with at least a portion of humerus 12 and generating a model of humerus 12 from the image data. Guide 50 preferably includes a base portion 52 including a contact surface shaped to substantially match an outer surface of a neck portion 13 of humerus 12, at least one proximal stabilization member 54 extending medially from base portion 52 and having a contact surface 56 shaped to substantially match an outer surface 11 of a head portion 14 of humerus 12, and at least one distal stabilization member 53 includes a contact surface shaped to substantially match an outer surface of a shaft portion 17 of humerus 12. The method further includes providing the guide 50 with a guide slot 68 for directing movement of the surgical instrument, wherein creating the contact surfaces of base portion 52, at least one proximal stabilization member 54, and at least one distal stabilization member 53 includes shaping the contact surfaces based on the model of the humerus 12 generated from the image data.

Figure 6:
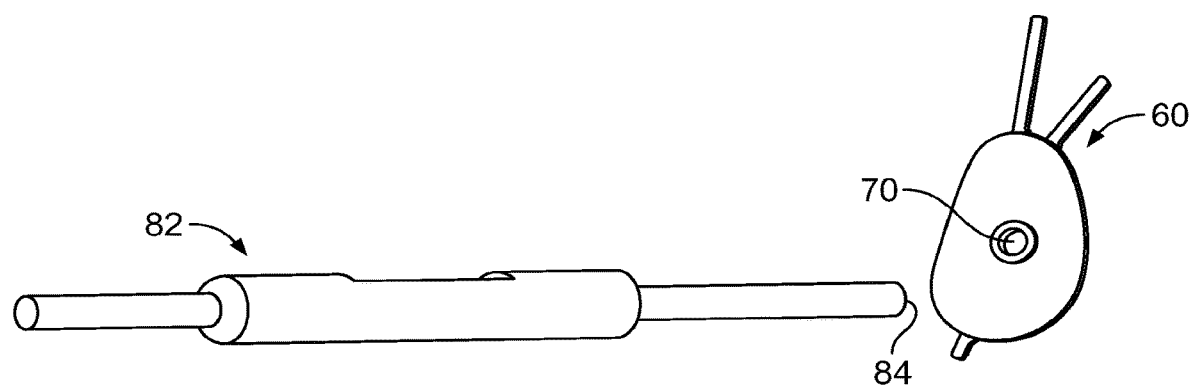
FIG. 6 is a view of an embodiment of a patient-specific cutting guide of the present invention for resecting the glenoid.
Figure 7:
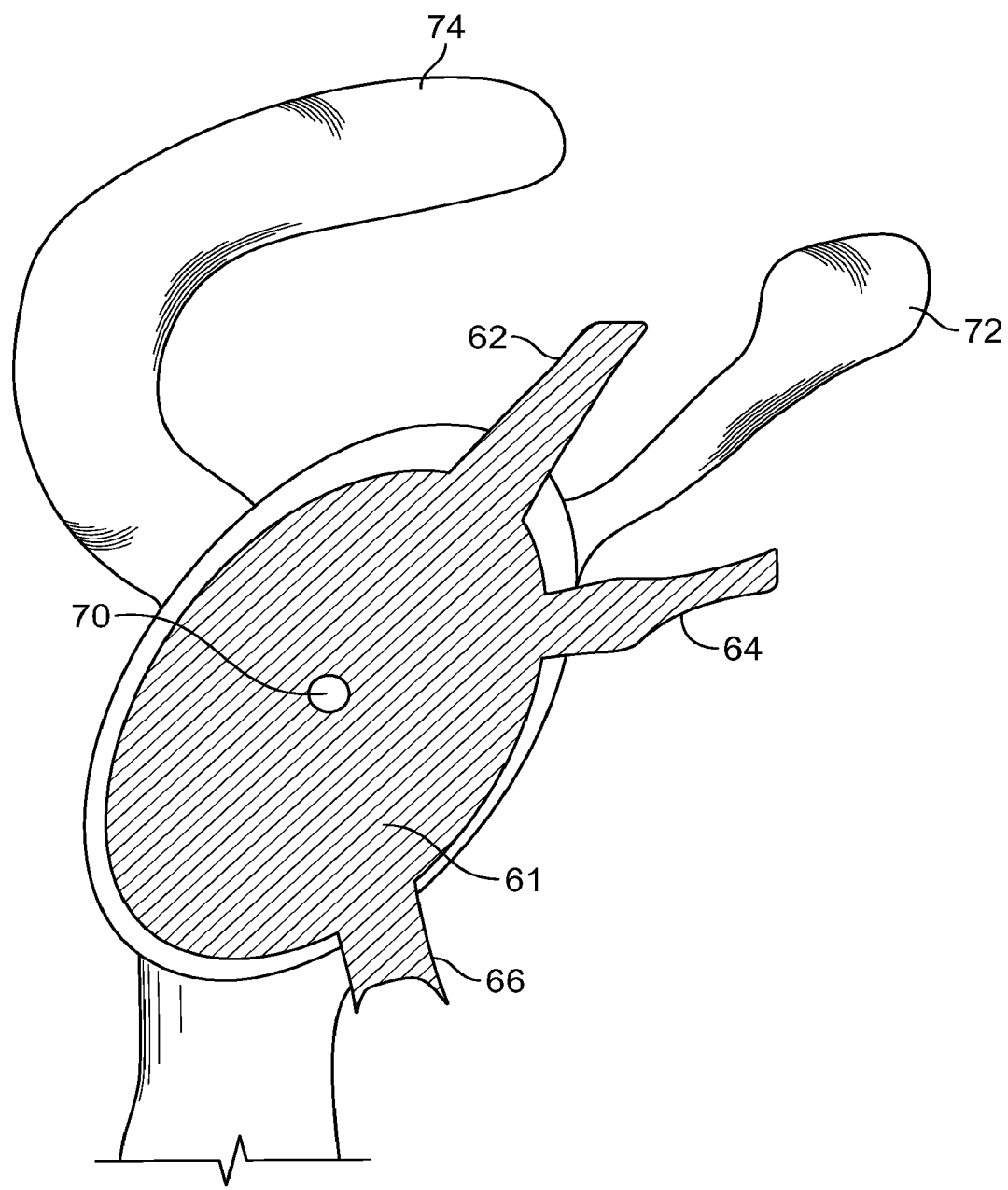
FIG. 7 is a view of the glenoid patient-specific cutting guide shown in FIG. 6 received in a glenoid cavity of a patient.
Figure 8:
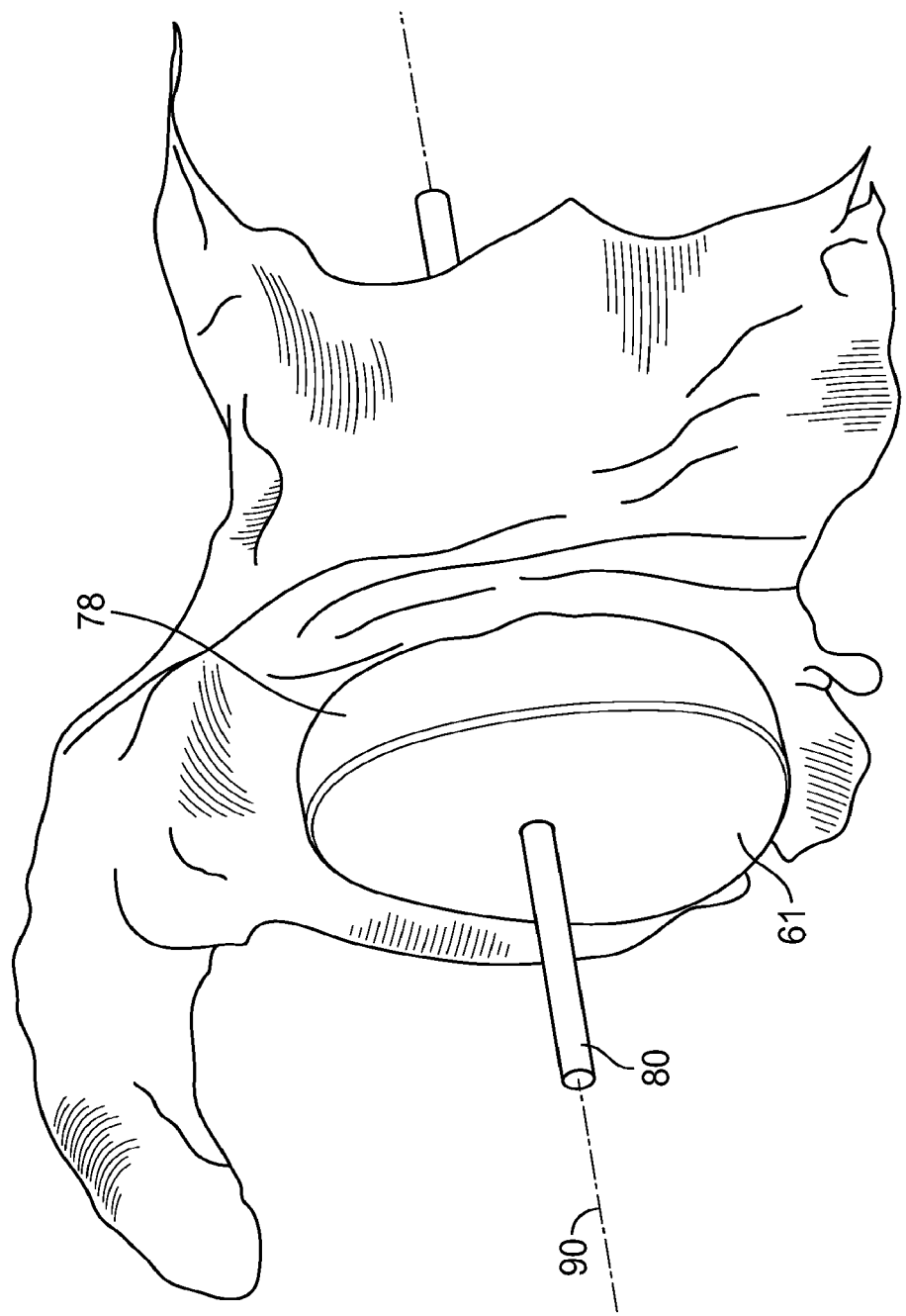
FIG. 8 is an alternate view of the cutting guide shown in FIG. 6 received in the glenoid cavity of a patient.

FIGS. 6-8 show patient-specific cutting guide 60 for guiding a surgical instrument 80 for resecting a portion of glenoid 20 of a patient. Guide 60 includes a base portion 61 having a contact surface 78 shaped to substantially match at least a portion of a cavity 21 of glenoid 20. Base portion 61 includes a guide hole 70 extending therethrough. Guide hole 70 has an axis 90 coaxial with an axis of rotation. Guide pin 80 engages bone of cavity 21 after passing through guide hole 70 of base portion 61. Placement of guide pin 80 may be aided by surgical instrument 82 having a cannula 84. Guide hole 70 is preferably aligned with the centerline of the spine of the scapula such that guide pin 80 has the correct location and orientation once engaged to bone in cavity 21. Once guide pin 80 is correctly positioned, surgical instrument 82 and guide 60 are removed and guide pin 80 can be used to guide drilling of a guide recess (not shown) in cavity 21 used to accept a central screw or peg 48 protruding outwardly from a glenoid component 46 as shown in FIG. 9.

Guide 60 preferably includes stabilization members 62, 64, 66 extending outwardly from base portion 61 and having a contact surface shaped to substantially match an outer surface of a portion of a scapula 22 of the patient. Stabilization member 62 is preferably located right of the acromial process 74 and left of the coracoid process 72 and stabilization member 64 is preferably located right of the coracoid process 72 when guide 60 is correctly positioned in the cavity of the glenoid.

Contact surface 78 of base portion 61 preferably includes at least one shaped protrusion (not shown) configured to contact a unique anatomical feature in cavity 21 of glenoid 20 of the patient. In use, guide 60 can be rotated within cavity 21 of glenoid 20 until the at least one shaped protrusion on contact surface 78 of base portion 61 keys into the unique anatomical feature in cavity 21 of glenoid 20.

One method of making patient-specific cutting guide 60 for guiding pin 80 used in guiding the resection of a portion of glenoid 20 includes obtaining image data associated with at least a portion of glenoid 20 and generating a model of glenoid 20 from the image data. Guide 60 preferably includes a base portion 61 with a contact surface 78 shaped to substantially match at least a portion of the glenoid cavity 21, the base portion 61 having a guide hole 70 extending therethrough, the guide hole 70 having an axis 90 coaxial with an axis of rotation. Guide 60 preferably further includes stabilization members 62, 64, 66 extending outwardly from base portion 61 each having a contact surface shaped to substantially match an outer surface of a portion of scapula 22. Contact surface 78 of base portion 61 and the contact surfaces of stabilization members 62, 64, 66 are created by shaping the contact surfaces based on the model of glenoid 20 generated from the image data.

After humerus 12 and glenoid 20 are resected, an example of a total shoulder arthroplasty prosthesis 100, as shown in FIG. 9, may be implanted. Humeral stem component 40 is preferably implanted into shaft 17 of humerus 12 with a bottom surface of flange 42 thereof lying adjacent flat resected surface 32 substantially co-axial with resection line 30. Glenoid component 46 is implanted into cavity 21 of glenoid 20 with central screw or peg 48 passing through an aperture in component 46 and into a guide recess created by the surgical instrument 80 being guided through guide hole 70 of guide 60.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a glenoid of a shoulder joint of a patient for a shoulder arthroplasty procedure, the method comprising:
   positioning a first contact surface of a base portion of a cutting guide into contact with a first surface of the glenoid that forms a cavity, the first contact surface being patient-specific and shaped to match the first surface of the glenoid;
   positioning a first stabilization member in contact with a first surface of a scapula of the patient, the first stabilization member extending from the base portion of the cutting guide and having a second contact surface being patient-specific and shaped to match the first surface of the scapula;
   positioning a second stabilization member in contact with a second surface of the scapula, the second stabilization member extending from the base portion of the cutting guide and having a third contact surface being patient-specific and shaped to match the second surface of the scapula;
   wherein while the first contact surface of the base portion is in contact with the first surface of the glenoid, a coracoid process of the patient is positioned between the first stabilization member and the second stabilization member, and wherein: the first and second stabilization members comprise a first edge, a second edge, and a longitudinal axis extending from the base portion and along a mid-point between the first edge and the second edge, and the first and second stabilization members are asymmetrical about the longitudinal axis.

2. The method of claim 1, wherein the base portion of the cutting guide has a guide hole extending therethrough.

3. The method of claim 2, further comprising inserting a guide pin through the guide hole and into the first surface of the glenoid.

4. The method of claim 3, wherein the guide hole is aligned with an axis of rotation of the shoulder joint while inserting the guide pin through the guide hole.

5. The method of claim 3, wherein the guide hole is aligned with a centerline of a spine of the scapula while inserting the guide pin through the guide hole.

6. The method of claim 3, further comprising removing the cutting guide from the glenoid while the guide pin remains in the first surface of the glenoid.

7. The method of claim 6, further comprising drilling a guide recess in the first surface of the glenoid, the drilling being guided by the guide pin.

8. The method of claim 7, further comprising inserting a screw or peg of a glenoid prosthesis into the guide recess in the first surface of the glenoid.

9. The method of claim 1, further comprising:
   while positioning the first contact surface of the base portion into contact with the first surface of the glenoid, rotating the cutting guide until the first contact surface uniquely keys to the first surface of the glenoid.

10. The method of claim 1, further comprising:
    positioning a third stabilization member in contact with a third surface of the scapula, the third stabilization member extending from the base portion of the cutting guide and having a fourth contact surface being patient-specific and shaped to match the third surface of the scapula.

11. The method of claim 1, further comprising manufacturing the cutting guide prior to using the cutting guide.

12. The method of claim 11, wherein manufacturing the cutting guide includes obtaining image data associated with the glenoid of the patient.

13. The method of claim 12, wherein manufacturing the cutting guide includes generating a model of the glenoid of the patient from the image data.

14. The method of claim 1, wherein the first contact surface is contoured to match a contour of the first surface of the glenoid, the first surface of the glenoid being an unresected surface of the glenoid.

15. The method of claim 1, wherein the second contact surface and third contact surface are each contoured to match a contour of the respective first and second surfaces of the scapula, the first and second surfaces of the scapula each being an unresected surface of the scapula.

16. A method of preparing a glenoid of a shoulder joint of a patient for a shoulder arthroplasty procedure, the method comprising:
    positioning a first contact surface of a base portion of a cutting guide into contact with a first surface of the glenoid that forms a cavity, the first contact surface being patient-specific and shaped to match the first surface of the glenoid, wherein the base portion of the cutting guide has a guide hole extending therethrough;
    positioning a first stabilization member in contact with a first surface of a scapula of the patient, the first stabilization member extending from the base portion of the cutting guide and having a second contact surface being patient-specific and shaped to match the first surface of the scapula;
    positioning a second stabilization member in contact with a second surface of the scapula, the second stabilization member extending from the base portion of the cutting guide and having a third contact surface being patient-specific and shaped to match the second surface of the scapula,
    wherein while the first contact surface of the base portion is in contact with the first surface of the glenoid, a coracoid process of the patient is positioned between the first stabilization member and the second stabilization member;
    inserting a guide pin through the guide hole and into the first surface of the glenoid;
    removing the base portion of the cutting guide from the glenoid while the guide pin remains in the first surface of the glenoid;
    drilling a guide recess in the first surface of the glenoid, the drilling being guided by the guide pin; and
    inserting a screw or peg of a glenoid prosthesis into the guide recess in the first surface of the glenoid.

17. A method of preparing a glenoid of a shoulder joint of a patient for a shoulder arthroplasty procedure, the method comprising:
    positioning a first contact surface of a base portion of a cutting guide into contact with a first surface of the glenoid that forms a cavity, the first contact surface being patient-specific and shaped to match the first surface of the glenoid;
    while positioning the first contact surface of the base portion into contact with the first surface of the glenoid, rotating the cutting guide until the first contact surface uniquely keys to the first surface of the glenoid;
    positioning a first stabilization member in contact with a first surface of a scapula of the patient, the first stabilization member extending from the base portion of the cutting guide and having a second contact surface being patient-specific and shaped to match the first surface of the scapula;

positioning a second stabilization member in contact with a second surface of the scapula, the second stabilization member extending from the base portion of the cutting guide and having a third contact surface being patient-specific and shaped to match the second surface of the scapula, wherein while the first contact surface of the base portion is in contact with the first surface of the glenoid, a coracoid process of the patient is positioned between the first stabilization member and the second stabilization member.

* * * * *